United States Patent [19]

Brois et al.

[11] 4,277,354
[45] Jul. 7, 1981

[54] OIL-SOLUBLE HYDROCARBYL SUBSTITUTED 1-AZA-3,7-DIOXABICYCLO[3.3.0]OCT-5-YL METHYL ALCOHOLS, AS ADDITIVES FOR FUNCTIONAL FLUIDS

[75] Inventors: Stanley J. Brois, Spring, Tex.; Jack Ryer, East Brunswick; Esther D. Winans, Colonia, both of N.J.

[73] Assignee: Exxon Research & Engineering Co., Florham Park, N.J.

[21] Appl. No.: 109,997

[22] Filed: Jan. 7, 1980

Related U.S. Application Data

[60] Continuation-in-part of Ser. No. 962,977, Nov. 22, 1978, which is a continuation-in-part of Ser. No. 752,872, Dec. 20, 1976, abandoned, and Ser. No. 752,873, Dec. 20, 1976, Pat. No. 4,069,023, which is a division of Ser. No. 573,545, May 1, 1975, Pat. No. 4,017,406.

[51] Int. Cl.$^3$ .............................................. C10M 1/32
[52] U.S. Cl. ................................ 252/51.5 R; 252/77; 252/390
[58] Field of Search .................... 252/51.5 R, 77, 390

[56] References Cited

U.S. PATENT DOCUMENTS

| 2,905,644 | 9/1959 | Butter ............................ 252/51.5 R |
| 3,025,313 | 3/1962 | Gunderson ...................... 252/390 X |
| 3,523,123 | 8/1970 | Wehrmeister ................... 252/390 X |
| 3,759,942 | 9/1973 | Himics ............................. 548/218 |
| 3,838,164 | 9/1974 | Himics ........................... 548/218 X |
| 3,915,970 | 10/1975 | Limaye et al. ............ 252/51.5 R X |
| 4,017,406 | 4/1977 | Brois et al. ................ 252/51.5 R X |
| 4,049,564 | 9/1977 | Ryer et al. ................. 252/51.5 R X |
| 4,199,463 | 4/1980 | Ryer et al. ................. 252/51.5 R X |

Primary Examiner—Andrew Metz
Attorney, Agent, or Firm—R. A. Dexter; J. J. Mahon

[57] ABSTRACT

Oil-soluble 2 and/or 8 alkyl substituted 1-aza-3, 7-dioxabicyclo [3.3.0] oct-5-yl methyl alcohols which are the reaction products of an aldehyde and tris [hydroxymethyl] aminomethane (THAM) are mineral oil additives which feature activity in automatic transmission fluid as copper alloy corrosion inhibitors.

6 Claims, No Drawings

OIL-SOLUBLE HYDROCARBYL SUBSTITUTED 1-AZA-3,7-DIOXABICYCLO[3.3.0]OCT-5-YL METHYL ALCOHOLS, AS ADDITIVES FOR FUNCTIONAL FLUIDS

This is a continuation-in-part of U.S. patent application Ser. No. 962,977 filed Nov. 22, 1978 which is a continuation-in-part of U.S. Ser. No. 752,872 filed Dec. 20, 1976, now abandoned, which was a division of U.S. Ser. No. 573,545 filed May 1, 1975, now U.S. Pat. No. 4,017,406 and Ser. No. 752,873, filed Dec. 20, 1976, now U.S. Pat. No. 4,069,023, also a division of said Ser. No. 573,545.

BACKGROUND OF THE INVENTION

1. Field of the Invention

The invention relates to oil-soluble hydrocarbyl substituted bicyclic oxazolidines, i.e. 1-aza-3,7-dioxabicyclo [3.3.0]oct-5-yl methyl alcohols, particularly those substituted in the 2 and/or 8 positions with a group preferably of at least 3 carbon atoms, which alcohols are derived from the reaction of an aldehyde and tris (hydroxymethyl) aminomethane.

These oil-soluble compounds have utility as additives for functional fluids, preferably mineral oil compositions and systems including automatic transmission fluids, lubricating oils and synthetic lubricants.

2. Description of the Prior Art

Lubricant additives derived from a reaction with tris (hydroxymethyl) aminomethane (THAM) are well known and include U.S. Pat. Nos.: 3,576,743; 3,632,511; 3,679,428; and 4,049,564 and United Kingdom Specification Nos.: 809,001 and 984,409.

In British Patent No. 564,506, the condensation product of THAM and formaldehyde, i.e. 1-aza-3,7-dioxabicyclo [3.3.0]oct-5-yl methyl alcohols, is said to react with fatty acids to give unstable ester products which are useful as drying oils.

U.S. Pat. No. 3,738,992 discusses esters of 1-aza-3,7-dioxabicyclo[3.3.0]oct-5-yl methyl alcohol as antifoam agents and lubricant additives, especially for aqueous textile lubricants.

U.S. Pat. No. 3,843,726 teaches that azadioxabicyclo-octane compounds, e.g. 1-aza-5-hydroxymethyl-2,8-diphenyl-3,7-dioxabicyclo (3.3.0) octane [see Example 1], (prepared by reaction of THAM and an aldehyde) can be halogenated to provide an intermediate useful for the preparation of an antiradiation drug.

Bicyclic oxazolidines are disclosed to be produced from an aldehyde and THAM in a publication entitled Chemistry and Use of Aminohydroxy Compounds by Commercial Solvents Corporation, N.Y. N.Y.

In prime movers utilizing a functional fluid for power transmission, including hydraulic fluids and automatic transmission fluids, it is generally necessary to remove heat generated during the operation of the functional fluid. One approach involves passing said fluid through a heat exchanger utilizing copper as a structural part or in a brazing mixture joining structural parts, e.g. the automatic transmission fluid of a car is frequently controlled by a heat exchanger located in the car radiator and immersed in the radiator coolant. Operational corrosion of the copper results in mechanically catastrophic intermixing of the functional fluid and radiator coolant (ethylene glycol) and/or loss of said fluid. It is necessary to reduce the copper corrosiveness of said fluid circulating in contact with copper so as to extend the operational lifetime of the prime mover or other mechanical device employing said fluid. One approach is to incorporate a compatible anti-copper corrosion additive into said fluid.

It is an object to this invention to provide an anti-copper-corrosion additive for functional fluids, preferably for automatic transmission fluids.

SUMMARY OF THE INVENTION

It has now been discovered that oil-soluble hydrocarbyl substituted analogues of 1-aza-3,7-dioxabicyclo[3.3.0] oct-5-yl methyl alcohols preferably in both the 2 and 8 positions, impart excellent anti-copper-corrosion activity to mineral oils and are particularly stable when added in at least a copper-corrosion reducing amount to a functional fluid, preferably a mineral oil system useful as an automatic transmission fluid (ATF) for prime movers.

In our pending U.S. patent application Ser. No. 962,977 two oil-soluble hydrocarbyl substituted bicyclic oxazolidines are disclosed as intermediates in the preparation of carboxylate esters of 1-aza-3,7-dioxabicyclo[3.3.0] oct-5-yl methyl alcohols, i.e. 1-aza-3,7-dioxa-2,8-di-n-propyl bicyclo [3.3.0]oct-51-yl methyl alcohol in Example 8 and 1-aza-3,7-dioxa-2,8-diphenyl-bicyclo[3.3.0]oct-5-yl methyl alcohol in Example 9. It has been discovered that oil-soluble precursors of said oil-soluble carboxylate esters impart anti-copper corrosion activity to mineral oils comparable to that of said esters while having excellent stability.

The oil-soluble additives of the invention can be characterized by the formulas:

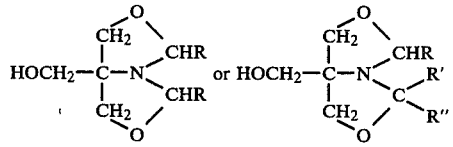

wherein R represents hydrogen and $C_1$ to $C_{30}$ hydrocarbyl substituent and R' and R" may be same or different and are each $C_1$ to $C_7$ hydrocarbyl groups, e.g. methyl, ethyl, t-butyl, phenyl, etc. The said additives of the invention are obtained from the reaction of 1 molar proportion of tris-(hydroxymethyl) aminomethane (THAM), with at least 2 molar proportions of a $C_1$ to $C_{30}$ substituted aldehyde or, with the combination of 1 molar proportion of said aldehyde and 1 molar portion of a ketone containing from 3 to 15 carbons.

Thus according to this invention there is produced a lubricating oil composition comprising a major amount of lubricating oil having dissolved therein at least a copper corrosion reducing amount of an oil-soluble reaction product of:
(a) about 1 molar proportion of tris-(hydroxymethyl) aminomethane and (b) at least 2 molar proportions of an aldehyde or the combination of 1 molar proportion of a ketone and 1 molar proportion of an aldehyde.

SYMMETRICAL ALDEHYDE-THAM ADDUCTS

The bicyclic oxazolidine methyl alcohols, more specifically 1-aza-3,7-dioxabicyclo[3.3.0]oct-5-yl methyl alcohols (I), also identified as aldehyde/THAM adducts can be readily prepared by condensing two moles of aldehyde with one mole of THAM.

Equation 1

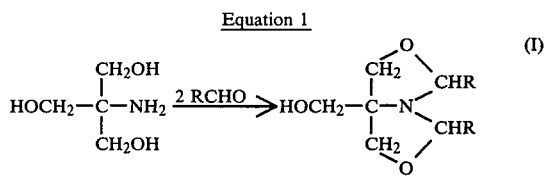

wherein R=CH₃,N—C₃H₇, i—C₃H₇,N—C₅H₁₁, i—C₅H₁₁,Ph,PhCH₂, etc. according to the procedures described by M. Senkus in the Journal of the American Chemical Society, 67, 1515 (1945). Thus, a variety of aldehydes such as valeraldehyde, propionaldehyde, butyraldehyde, isobutaldehyde, 2-ethyl-hexanal, dodecyl aldehyde, benzaldehyde, tolualdehyde, naphthaldehyde, phenylacetaldehyde, etc., can be condensed with (THAM) to produce symetrically substituted aldehyde/THAM adducts wherein R=R.

For these symmetrical as well as the unsymmetrical adducts at least one hydrocarbyl substituents group in the 2 or 8 position preferably has at least 3 carbon atoms for improved stability and oil solubility.

UNSYMMETRICAL ALDEHYDE-THAM ADDUCTS

In another additive embodiment of the present invention, unsymmetrical adducts may be prepared by first treating THAM with one mole of ketone (Equation 2) to generate an oxazoline product (II) according to procedures described in the literature by E. D. Bergmann, Chemical Reviews, 53, 309 (1953).

Equation 2

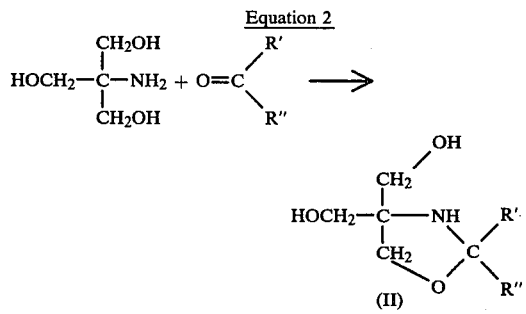

wherein R' and R'' may be the same or different and represent a $C_1$ to $C_7$ hydrocarbyl substituent. Subsequent treatment of the oxazolidine [II] with a mole of aldehyde affords the unsymmetrical adduct III, as depicted in Equation 3.

Equation 3

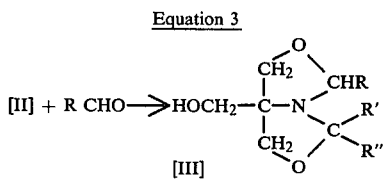

wherein R, R' and R'' are as earlier described.

Aldehyde reactants described in the preparation of symmetrically substituted adducts (I) above are suitable for the reactions described in Equation 3.

Numerous types of ketone reactants can be employed in the formation of the oxazolidines (Equation 2) required in the design of unsymmetrically substituted 1-aza-3,7-dioxabicyclo [3.3.0]oct-5-yl methyl alcohols (III). Included in the repertory of useful having ketones from 3 to 15 carbons are acetone, butanone, pentanones, methyl isobutyl ketone, amyl methyl ketone, acetophenone, etc.

In forming unsymmetrical adducts (III) from oxazolidine generated from ketone reactants, a particularly preferred aldehyde is formaldehyde which, owing to its favorable steric requirements, rapidly cyclizes to the oxazolidine intermediate [II] to the desired bicyclic structure, III wherein R is H.

The following preparations and examples are included herein as further description and illustrative of the present invention.

PREPARATION OF ALDEHYDE-THAM ADDUCTS

EXAMPLE 1

1-aza-3,7-dioxabicyclo[3.3.0]oct-5-yl methyl alcohol 0.1 mole (12.1 g) of THAM was dissolved in an equal weight of water. To the resulting solution in a 250 ml. Erlenmeyer flask equipped with magnetic stirrer was added 0.2 mole (6.0 g) of paraformaldehyde. The stirred mixture was heated to 70° C. to effect dissolution of the paraformaldehyde and continued for 15 minutes at 70° C. to produce the 1-aza-3,7-dioxabicyclo [3.3.0]oct-5-yl methyl alcohol (hereinafter called DOBO) in quantitative yields. The product after evaporation of water and recrystallization from benzene melted at 60° C.–61° C. and analyzed for 49.12% carbon, 7.52% hydrogen and 9.59% nitrogen. This product was not oil-soluble.

EXAMPLE 2

1-aza-3,7,dioxa-2,8-dipropyl-bicyclo[3.3.0]oct-5-yl methyl alcohol 1.5 moles (181.5 g) of tris-(hydroxymethyl) aminomethane (THAM) and 3.0 moles (216 g) of n-butyraldehyde were added to 200 ml of benzene in a liter flask provided with a Dean Stark trap to collect evolved water. The reactants were heated for 5 hours at from 78° C. to 102° C. with the collection of 54 cc of water. The benzene was then distilled off and the resulting clear-yellow viscous residue was vacuum distilled at 99° to 105° C. and 0.08–0.1 mm pressure. The product analyzed for 62.7% C, 10.1% H and 6.1% nitrogen.

EXAMPLE 3

1-aza-3,7-dioxa-2,8-di-isopropyl-bicyclo[3.3.0]oct-5-yl methyl alcohol.

The procedure of Example 2 was generally followed except 2 moles (242 g) of THAM and 4.1 moles (296 g) of isobutyraldehyde was admixed with 400 ml of benzene. 65 cc of water was collected after distillation, product, a colorless oil, analyzed for 62.6% C, 9.6% H and 6.1% N.

EXAMPLE 4

1-aza-3,7-dioxa-2,8-diphenyl bicyclo[3.3.0]oct-5-yl methyl alcohol

The procedure of Example 3 was generally followed except 3 moles (318 g) of benzaldehyde was substituted for the isobutyraldehyde, 1.5 moles of THAM was used, xylene was used instead of benzene and heating was at 110° to 155° C. After recrystallization from ether the product, a white solid, analyzed for 72.6% C, 6.4% H and 4.4% N.

EXAMPLE 5

1-aza-3,7 dioxa-2,8-dihexyl-bicyclo[3.3.0]oct-5-yl methyl alcohol 0.5 mole (60.2 g) of THAM and 1.05 moles of heptaldehyde were admixed, the temperature rose to 48° C. After stirring overnight 125 ml toluene was added and the mixture refluxed resulting in removal of 17 cc $H_2O$ by collection in the Dean-Stark trap. The toluene was blown off at 150° C. and the mixture vacuum distilled at 150° C. and 0.03 mm pressure producing a colorless oil that analyzed for 69.5% C, 11.3% H and 4.5% N.

The oil-soluble additives of this invention can be incorporated into a wide variety of functional fluid. They are preferably used in lubricating oil compositions, such as automotive crankcase lubricating oils, automatic transmission fluids, etc., and at concentrations generally within the range of about 0.01 to 1%, preferably 0.05 to 0.5, weight percent, of the total composition. Other functional fluids to which the additives can be added include not only mineral oil based fluids, but also fluids based on: lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; and, mixtures of mineral oil and synthetic oil in any proportion, etc.

When the oil-soluble additives of this invention are used as anti-cooper-corrosion additives for automatic transmission fluids (ATF), it has been found that these additives do not deteriorate the frictional properties of the ATF, i.e. these additives are compatible in ATF. The ATF lubricants contain many other additives which are typically blended into the lubricating mineral oil at the following range of treating levels.

| Components | Concentration range, vol. % |
|---|---|
| V.I. improver | 1–15 |
| Metal Corrosion inhibitor (includes Cu) | 0.01–1 |
| Oxidation inhibitor | 0.01–1 |
| Dispersant | 0.5–10 |
| Pour Point Depressant | 0.01–1 |
| De-emulsifier | 0.001–0.1 |
| Anti-foaming agent | 0.001–0.1 |
| Anti-wear agent | 0.001–1 |
| Seal swellant | 0.1–5 |
| Friction modifier | 0.01–1 |
| Mineral Oil | Balance |

The following data is illustrative of the copper corrosion inhibition improvement of ATF lubricants afforded according to this invention.

Two commercial ATF lubricants I and II were examined in the following copper corrosion test in both modified and unmodified form. The copper corrosion test is carried out as follows: A copper specimen $3 \times \frac{1}{2} \times 1/16$ inches is polished until clean and uniform, washed in hexane, dried and weighed to the tenth of a milligram. 40 cc of the test fluid is placed in a test tube into which the copper bar is immersed, and the test tube thereafter corked with a cork with two $\frac{1}{8}$ inch holes in it. The tube is placed in a 300° F. aluminum block for 65 hours. At the end of the time, the specimen is removed, washed in hexane, rubbed vigorously with a paper towel to remove any loose deposits, rewashed and reweighed.

TABLE II

| Copper Corrosion Tests, mg. lost in 65 hours | | |
|---|---|---|
| ATF Lubricant | ATF I | AFT II |
| Unmodified | 15.21 | 14 |
| Modified by addition of 0.2 wt.% of Product of Example 2 | 14 | 7 |
| Modified by addition of 0.3 wt.% of Product of Example 2 | 2 | — |

The additive product of Example 3 was incorporated into an ATF formulation at a 0.09 wt.% concentration (based on the entire weight of the ATF formulation) as an anti-copper-corrosion inhibitor. The resulting ATF formulation passed the L-2 Friction Test required by the Buick Division of General Motors Corporation and conducted on S.A.E. No. 2 friction apparatus which showed the additive of the invention had no adverse effect on the friction characteristics of the ATF; a deemulsibility test; and passed the difficult Turbo Hydromatic Transmission Cycling Test—which is a copper braxe corrosion test published in Dexron II Automatic Transmission Fluid Specification by General Motors Co., Detroit, Michigan (see Pub No. 6137-M 2nd Ed. July 1978, Appendix Page 35). Long chain aldehydes and ketones i.e. chains greater than 30 carbons, formed in the oxidation of copolymers of ethylene and propylene, butylene and isobutylene, and ethylene propylene and 1,4-hexadiene can also be employed for multifunctionality where dispersancy is desired. The aldehyde and ketone functionalized polymers will have average molecular weights within the range of about 350 to about 100,000.

The invention in its broader aspect is not limited to the specific details shown and described and departures may be made from such details without departing from the principles of the invention and without sacrificing its chief advantages.

What is claimed is:

1. A composition comprising a major amount of a functional fluid being an oil of lubricating viscosity and a minor but at least a copper-corrosion inhibiting amount of an oil-soluble hydrocarbyl substituted bicyclic oxazolidine.

2. A composition according to claim 1 wherein said functional fluid is an automatic transmission fluid comprising a major amount of a mineral lubricating oil and said oxazolidine is characterized by the formulas:

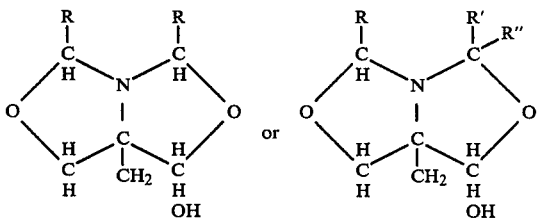

wherein R represents hydrogen and $C_1$ to $C_{30}$ hydrocarbyl substituent and R' and R'' may be same or different and are each a $C_1$ to $C_7$ hydrocarbyl group.

3. A composition according to claim 2 wherein said functional fluid is a mineral oil base automatic transmission fluid and said oxazolidine is obtained from the reaction of 1 molar proportion of tris-(hydroxymethyl) aminomethane with at least 2 molar proportions of a $C_1$ to $C_{30}$ substituted aldehyde or the combination of 1 molar proportion of said aldehyde and 1 molar proportion of a ketone containing from 3 to 15 carbons.

4. A composition according to claim 2 wherein said oxazolidine is 1-aza-3,7-dioxa-2,8-di-isopropyl-bicyclo[3.3.0]oct-5-yl methyl alcohol present in an amount ranging from 0.01 to 1 weight percent based on the total weight of said composition.

5. A composition according to claim 2 wherein said oxazolidine is 1-aza-3,7-dioxa-2,8-diphenyl bicyclo[3.3.0]oct-5-yl methyl alcohol present in an amount ranging from 0.01 to 1 weight percent based on the total weight of said composition.

6. A composition according to claim 2 wherein said oxazolidine is 1-aza-3,7-dioxa-2,8-dipropyl-bicyclo[3.3.0]oct-5-yl methyl alcohol present in an amount ranging from 0.01 to 1 weight percent based on the total weight of said composition.

* * * * *